United States Patent [19]

Finnan

[11] Patent Number: 4,639,533
[45] Date of Patent: Jan. 27, 1987

[54] ALPHA TOCOPHEROL PROCESS

[75] Inventor: Jeffrey L. Finnan, Southgate, Mich.

[73] Assignee: BASF Corporation, Wyandotte, Mich.

[21] Appl. No.: 403,085

[22] Filed: Jul. 29, 1982

[51] Int. Cl.$^4$ .......................................... C07D 311/72
[52] U.S. Cl. .................................................... 549/411
[58] Field of Search ............................... 549/411, 410

[56] References Cited

U.S. PATENT DOCUMENTS

| 4,191,692 | 3/1980 | Grafen et al. | 549/411 |
| 4,208,334 | 6/1980 | Fitton et al. | 549/411 |
| 4,217,285 | 8/1980 | Yoshino et al. | 549/411 |

Primary Examiner—Nicky Chan
Attorney, Agent, or Firm—Rupert B. Hurley, Jr.; Joseph D. Michaels

[57] ABSTRACT

D,1-alpha-tocopherol can be prepared by reacting trimethylhydroquinone and a phytyl derivative such as phytol or isophytol in the presence of a Lewis acid, a strong acid and an amine.

19 Claims, No Drawings

ALPHA TOCOPHEROL PROCESS

BACKGROUND OF THE INVENTION

1. Field of the Invention

This invention relates to an improved process for manufacturing d,l-alpha-tocopherol.

2. Description of the Prior Art

The preparation of d,l-alpha-tocopherol by the condensation of trimethylhydroquinone and a phytol derivative in the presence of an inert solvent and acid condensing agents is well known in the art. The acid catalyst can be either or both a Lewis acid such as zinc chloride or a strong inorganic acid such as hydrochloric acid, sodium bisulfate or para-toluenesulfonic acid. In addition, it is known from U.S. Pat. No. 4,191,692 to pre-react isophytol with a small amount of ammonia or an amine prior to reaction with trimethylhydroquinone.

The use of zinc chloride, an inert solvent and gaseous hydrochloric acid in the process of producing d,l-alpha-tocopherol is disclosed by Karrer in U.S. Pat. Nos. 2,411,967; 2,411,968; and 2,411,969. Greenbaum et al in U.S. Pat. No. 3,708,505 also disclose the use of a combination of a Lewis acid and a strong acid in a process for the preparation of d,l-alpha-tocopherol.

Improved process catalysts or combinations thereof are also disclosed in U.S. Pat. Nos. 4,208,334; 2,723,278; 3,789.086; 3,459,773; 3,444,213; and 4,217,285.

SUMMARY OF THE INVENTION

It has been unexpectedly discovered that by including a small amount of an amine in the reaction mixture for the preparation of d,l-alpha-tocopherol that an improved product is obtained, specifically a product having greater purity. Additionally, the percent yield is also increased. In the process of the invention, trimethylhydroquinone and an inert organic solvent are charged into a reaction vessel together with a combination of at least one aprotic Lewis acid, at least one protonic strong organic acid, and at least one amine. A phytol derivative such as isophytol is then slowly added to the reaction mixture and when addition has been completed, the reaction mass is refluxed for a sufficient time to produce d,l-alpha-tocopherol. Optionally, acetic anhydride can be added to produce d,l-alpha-tocopherol acetate. It is a particular advantage of the present process that the synthesis is essentially a one-step process which produces a higher yield as well as a higher quality d,l-alpha-tocopherol.

DESCRIPTION OF THE PREFERRED EMBODIMENTS

The phytyl derivative useful as a reactant in the process of the invention has the formulas:

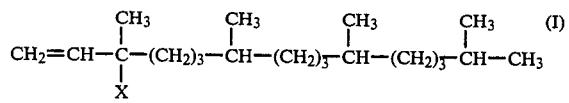

and

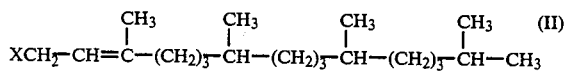

wherein X is a leaving group. Useful leaving groups include hydroxy, halogen, lower alkylsulfonyloxy, arylsulfonyloxy, lower alkoxy, and lower alkanoyloxy. The halogen-leaving groups are preferably chlorine and bromine. The preferred lower alkylsulfonyloxy leaving group is mesyloxy. The preferred arylsulfonyloxy leaving group is tosyloxy. The preferred lower alkanoyloxy group is acetoxy. The preferred lower alkoxy leaving groups are n-butoxy, methoxy, isobutoxy, and ethoxy.

As used throughout the specification, the term "halogen" includes all four halogens such as bromine, chlorine, fluorine and iodine.

The term "lower alkyl" includes saturated aliphatic hydrocarbon groups containing 1 to 7 carbon atoms such as methyl, ethyl, propyl, isopropyl, isobutyl, etc.

The term "lower alkoxy" includes lower alkoxy groups containing from 1 to 7 carbon atoms such as methoxy, ethoxy, n-butoxy, isobutoxy, etc.

The term "lower alkanoyl" includes lower alkanoyl groups containing from 1 to 7 carbon atoms, preferably from 2 to 7 carbon atoms such as acetyl, propionyl, etc.

The term "aryl" denotes monocyclic aromatic hydrocarbons such as phenyl and polycyclic aromatic hydrocarbons such as naphthyl which can be unsubstituted or substituted in one or more positions with a lower alkyl or nitro group.

Specific examples of phytol derivatives useful in the preparation of the alpha-tocopherols of the invention include phytol, isophytol, phytadiene, phytol chloride, phytol bromide, phytol acetate and phytol methyl ether. The preferred phytol is isophytol.

The inert organic solvents which can be employed as a reaction medium in the process of the invention are those aromatic and aliphatic hydrocarbon solvents having a boiling point below the boiling points of the reactants and the desired product. Preferred solvents include aliphatic hydrocarbon solvents having about 5 to about 12 carbon atoms. Representative aromatic hydrocarbon solvents include xylene, benzene, and toluene. Miscellaneous inert organic solvents also can be used. Representative aliphatic hydrocarbon solvents include pentane, hexane, heptane, octane, nonane, decane, undecane, and dodecane. Preferably, n-heptane is utilized. Other inert organic solvents can be used such as an aliphatic ether such as isopropyl ether.

The aprotic acids useful as catalysts in the process of the invention include boron trifluoride, boron tribromide, aluminum chloride, aluminum bromide, zinc chloride, boron trifluodiphosphoric acid complex, and the like. The preferred Lewis acid is zinc chloride.

Protonic strong acid catalysts useful in the process of the invention include hydrogen chloride gas, sulfuric acid, hydrochloric acid, nitric acid, para-toluene sulfonic acid, sodium bisulfate, and mixtures thereof. Preferably, strong acids such as sulfuric acid, para-toluene sulfonic acid, and sodium bisulfate are used. Especially preferred is anhydrous hydrogen chloride gas present in the reaction mixture in an amount sufficient to saturate said reaction mixture.

The amines which are useful in the process of the invention can be arylaliphatic amines having about 7 to about 24 carbon atoms or aliphatic and cycloaliphatic amines having about 7 to about 24 carbon atoms, preferably about 18 to about 22 carbon atoms, in the aliphatic chain. The amines can be primary, secondary or tertiary amines. The alkyl primary monoamines which can have straight or branched chains are preferred. Representative examples of useful alkyl amines are tridecylamine, l-docosanamine, l-eicosanamine, pentadecylmethylamine, octadecyldimethylamine, dioctyldecylamine, and octadecylamine. A representative example of a useful cycloaliphatic amine is cyclohexylamine. A representative example of a useful arylaliphatic amine is benzylamine. Amines useful in the process of the invention can be further substituted with groups such as hydroxy, lower alkoxy, or lower alkylamino groups.

The general reaction of the phytol derivative with trimethylhydroquinone is known in the art as indicated by the procedures provided in U.S. Pat. No. 3,708,505, incorporated herein by reference. The process of the invention is performed by charging trimethylhydroquinone into a reaction flask together with the Lewis acid, strong acid, amine, and inert organic solvent. The combination is then heated at a temperature of 50° C. to about 150° C. and the phytol derivative is added slowly to said combination of ingredients over a period of about 2 to about 6 hours. The reaction mass is then further heated at about 50° C. to about 150° C. for about 6 to about 24 hours. When the reaction is completed, the mass can be purified by distillation if so desired.

One of the useful and unexpected results of using the amine in combination with the Lewis acid and strong acid in accordance with the process of the invention is that the d,l-alpha-tocopherol produced has a purity of about 90 to about 95 percent by weight, which meets feed grade standards. Purification is, therefore, only required if the product is to meet national formulary standards. Alternatively, acetic anhydride can be added to the crude d,l-alpha-tocopherol obtained by the process of the invention in order to convert the tocopherol to d,l-alpha-tocopherol acetate.

The ratio of reactants is from about 0.9 to about 1.1 mole, preferably about 1.0 mole, of trimethylhydroquinone to about 0.9 to about 1.1 mole, preferably about 1.0 mole, of phytol derivative (preferably isophytol) in combination with 0.1 to 1.5 moles each, preferably 0.35 to 0.75 mole, of the Lewis acid and strong acid catalyst.

The amount of inert organic solvent present in the reaction mixture can vary, the minimal proportion necessary being that amount sufficient for the reaction to take place. Thus, the inert organic solvent can be present in the proportion of from 1 to 10 parts by weight per part by weight of the phytol derivative.

The amount of Lewis acid or strong acid catalyst can be from 0.04 part by weight, per part by weight of the phytyl derivative, up to very large amounts of 0.5 part by weight of the phytol derivative or more although large amounts provide no advantage.

The strong acid which is used can be an aqueous acid such as concentrated hydrochloric acid and concentrated hydrobromic acid or strong mineral acids such as sulfuric acid or sodium bisulfate. Hydrochloric acid is preferred, and it is especially preferred that instead of aqueous hydrochloric acid, that hydrogen chloride gas be employed. This can be passed into the reaction mixture during the reaction and maintained at a saturation concentration. The use of hydrogen chloride gas has the particular advantage that the acid concentration cannot rise excessively since hydrogen chloride gas present in excess of that required to saturate the reaction mixture volatilizes from the reaction mixture.

The following examples illustrate the various aspects of the invention but are not intended to limit its scope. Where not otherwise specified throughout this specification and claims, temperatures are given in degrees centigrade and parts, percentages, and proportions are by weight.

EXAMPLE 1

(Control, forming no part of this invention)

In this example, and in Example 2, the process of the prior art is shown in which isophytol is mixed and prereacted with an amine prior to reaction with trimethylhydroquinone.

Crude isophytol (97.5 percent by weight purity) in the amount of 100 parts by weight was mixed with 0.3 part by weight of tridecylamine and thereafter heated at 80° C. for two hours. After cooling, the product of the isophytylamine reaction was used directly in the condensation reaction with trimethylhydroquinone as described below.

The amine-isophytol reaction product was added dropwise to a mixture of trimethylhydroquinone (76.1 grams, 0.495 mole), zinc chloride 95 percent by weight aqueous (20.7 grams, 0.150 mole) in technical grade n-heptane (380 ml). The mixture was heated to constant reflux with a continuous hydrogen chloride sparge and the amine-isophytol reaction product (181 ml, 0.50 mole) was added dropwise over a period of 90 minutes. After completion of the addition of the amine-treated isophytol, the hydrogen chloride sparge was continued for an additional 15 minutes, and five minutes later the heating was stopped. After cooling for one hour, the reaction mixture was extracted with three portions (350 ml) of methanol/water (1:1), acidified with 1 ml of concentrated hydrochloric acid, and the heptane was evaporated under vacuum. The crude tocopherol was then reacted with acetic anhydride (200 ml), 2.1 mole for a period of four hours at reflux temperature. The resulting acetic acid and excess anhydride were removed under vacuum. The crude alpha-tocopherol acetate was assayed via gas chromatography to determine the yield and purity. The results are indicated in the following table.

EXAMPLE 2

(Control, forming no part of this invention)

Example 1 was repeated except that tridecyl amine was utilized to treat the isophytol by mixing one weight percent of said amine with 100 parts by weight of the crude isophytol of Example 1 and thereafter heating at 80° C. for two hours. The amine-treated isophytol was utilized in the same proportions and the same procedure was followed as described in Example 1.

EXAMPLE 3

Under a nitrogen atmosphere there were added to a reaction container 380 ml of technical grade n-heptane, 99.0 percent by weight trimethylhydroquinone (76.1 grams, 0.495 mole), 95 percent by weight zinc chloride (20.7 grams, 0.150 mole) and 0.3 weight percent of tridecylamine based upon the weight of the crude isophytol to be added subsequently, namely, 181 ml, 0.50 mole) of 97.5 percent isophytol. The mixture obtained was heated to constant reflux with a continuous hydrogen chloride sparge and then the isophytol was added over a 90 minute period. After completion of the isophytol addition, the hydrogen chloride sparge was continued for an additional 15 minutes, and five minutes later the heating was stopped. After cooling for a period of one hour, the reaction mixture was extracted with three portions (350 ml) of methanol/water (1:1) acidified with 1 ml of concentrated hydrochloric acid. The heptane reaction medium was evaporated under vacuum. The crude alpha-tocopherol was reacted with acetic anhydride (200 ml, 2.1 mole) for four hours at reflux temperature. The resulting acetic acid and excess acetic anhydride were removed under vacuum. The crude alpha-tocopherol acetate was assayed utilizing gas chromatography to determine the yield and purity. The results are shown in the table below.

EXAMPLE 4

Example 3 was repeated except that a proportion of one weight percent of tridecylamine was utilized based upon the weight of the crude isophytol used in the reaction.

EXAMPLE 5

The procedure and proportions of Example 3 were repeated except that octadecylamine was substituted for tridecylamine.

EXAMPLE 6

The procedure and proportions of Example 4 were repeated except that octadecylamine was substituted for tridecylamine.

EXAMPLES 7-10

The procedure and proportions of Example 4 are repeated except that 1-docosanamine, eicosanamine, octadecyldimethyl amine, and dioctadecylamine are substituted for tridecylamine.

TABLE

| Example | Amine | Amine Level (wt. % to Isophytol) | Premixed and Prereacted | Yield (% of Theory) | Purity (%) |
|---|---|---|---|---|---|
| 1 (control) | Tridecylamine | 0.3 | + | 95.3 | 94.4 |
| 2 (control) | Tridecylamine | 1.0 | + | 95.7 | 94.6 |
| 3 | Tridecylamine | 0.3 | − | 96.5 | 94.8 |
| 4 | Tridecylamine | 1.0 | − | 96.8 | 94.9 |
| 5 | Octadecylamine | 0.3 | − | 98.2 | 95.4 |
| 6 | Octadecylamine | 1.0 | − | 97.0 | 95.4 |

While this invention has been described with reference to certain specific embodiments, it will be recognized by those skilled in the art that many variations are possible without departing from the scope and spirit of the invention, and it will be understood that it is intended to cover all changes and modifications of the invention disclosed herein for the purposes of illustration which do not constitute departure from the spirit and scope of the invention.

The embodiments of the invention in which an exclusive property of privilege is claimed are defined as follows:

1. A process for producing alpha tocopherol comprising reacting, in the presence of an inert organic solvent, trimethylhydroquinone with a phytyl derivative selected from the group consisting of at least one of

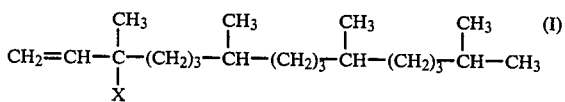

and

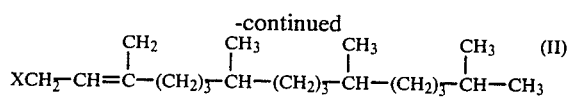

wherein X is a leaving group, in the presence of at least one aprotic Lewis acid, at least one protonic strong acid, and at least one amine having about 7 to about 24 carbon atoms.

2. The process of claim 1 wherein X is selected from the group consisting of arylsulfonyloxy, lower alkylsulfonyloxy, hydroxy, halogen, lower alkoxy, and lower alkanoyloxy.

3. The process of claim 2 wherein X is hydroxy.

4. The process of claim 2 or 3 wherein said amine is a primary, secondary or tertiary aliphatic, cycloaliphatic, or arylaliphatic amine.

5. The process of claim 4 wherein said amine is an aliphatic monoamine.

6. The process of claim 5 wherein said amine is selected from the group consisting of at least one of tridecylamine, octadecyldimethylamine, dioctyldecylamine, 1-docosanamine, 1-eicosanamine, and octadecylamine.

7. The process of claim 5 or 6 wherein said aprotic Lewis acid is selected from the group consisting of at least one of boron trifluoride, boron tribromide, aluminum chloride, aluminum bromide, zinc chloride, and boron trifluorophosphoric acid complex.

8. The process of claim 7 wherein said aprotic Lewis acid is zinc chloride.

9. The process of claim 7 wherein said protonic strong acid is selected from the group consisting of at least one of sulfuric acid, hydrochloric acid, hydrogen chloride gas, nitric acid, para-toluenesulfonic acid, and sodium bisulfate.

10. The process of claim 9 wherein said protonic strong acid is hydrochloric acid.

11. The process of claim 9 wherein said protonic strong acid is hydrogen chloride gas.

12. The process of claim 11 wherein the amount of hydrogen chloride gas present during the reaction is sufficient to saturate the reaction mixture.

13. The process of claim 9 or 12 wherein said inert organic solvent is an aliphatic or aromatic hydrocarbon or another inert organic solvent having a boiling point below the boiling points of the reactants and the desired product.

14. The process of claim 13 wherein said inert organic solvent is an aliphatic ether.

15. The process of claim 13 wherein said aromatic hydrocarbon is selected from the group consisting of at least one of xylene, benzene, and toluene.

16. The process of claim 13 wherein said inert organic solvent is selected from the group consisting of at least one of an aliphatic hydrocarbon having about 5 to about 12 carbon atoms, and an aromatic hydrocarbon.

17. The process of claim 16 wherein said aliphatic hydrocarbon solvent is selected from a group consisting of at least one of pentane, hexane, heptane, octane, nonane, decane, undecane, and dodecane.

18. The process of claim 17 wherein said inert organic solvent is n-heptane, said amine is octadecylamine, said aprotic Lewis acid is zinc chloride, said protonic strong acid is hydrogen chloride gas and said phytyl derivative is isophytol.

19. A process for producing alpha-tocopherol acetate comprising the process of producing alpha-tocopherol in accordance with the process of claims 2, 5, 8, 9, or 16 and additionally reacting the product obtained with acetic anhydride.

* * * * *